(12) United States Patent
Aharon

(10) Patent No.: US 8,882,752 B2
(45) Date of Patent: Nov. 11, 2014

(54) AESTHETIC TREATMENT DEVICE

(75) Inventor: Oren Aharon, Haifa (IL)

(73) Assignee: Epilady 2000 LLC, Hatzor Haglilit (IL)

(*) Notice: Subject to any disclaimer, the term of this patent is extended or adjusted under 35 U.S.C. 154(b) by 439 days.

(21) Appl. No.: 11/885,385

(22) PCT Filed: Mar. 3, 2005

(86) PCT No.: PCT/IL2005/000253
§ 371 (c)(1),
(2), (4) Date: May 27, 2008

(87) PCT Pub. No.: WO2006/092776
PCT Pub. Date: Sep. 8, 2006

(65) Prior Publication Data
US 2009/0054880 A1    Feb. 26, 2009

(51) Int. Cl.
*A61B 18/20* (2006.01)
*A61N 5/067* (2006.01)
*A61B 18/00* (2006.01)
*A61B 18/18* (2006.01)
*A61B 19/00* (2006.01)

(52) U.S. Cl.
CPC ..... *A61B 18/203* (2013.01); *A61B 2018/00005* (2013.01); *A61B 2018/00452* (2013.01); *A61B 2018/1807* (2013.01); *A61B 2019/306* (2013.01); *A61B 2019/461* (2013.01)
USPC ........ 606/9; 607/89; 607/90; 607/88; 606/10; 606/12; 128/898

(58) Field of Classification Search
CPC ........... A61B 2018/00452; A61B 2018/00005; A61B 2018/00458; A61B 2018/00636; A61B 2018/00642; A61B 2018/0066; A61B 2017/0022; A61B 2017/00057; A61B 18/203

USPC ..................... 606/2–19; 607/88–94; 128/898
See application file for complete search history.

(56) References Cited

U.S. PATENT DOCUMENTS 4,608,978 A    9/1986  Rohr
4,930,504 A *  6/1990  Diamantopoulos et al. .... 607/88
(Continued)

FOREIGN PATENT DOCUMENTS

WO    98/33556 A    8/1998
WO    99/58195 A   11/1999
WO    03/002187 A   1/2003

OTHER PUBLICATIONS

International Search Report for International Application No. PCT/IL05/00253 mailed Sep. 8, 2005.
(Continued)

*Primary Examiner* — Ahmed Farah
(74) *Attorney, Agent, or Firm* — Stein IP, LLC

(57) ABSTRACT

An aesthetic treatment device and method for treating the skin of a patient, the device comprising at least one of a plurality of arc lamps, each arc lamp provided with a reflector for obtaining a substantially collimated beam; a pulse generator for generating a train of pulses of electrical energy for energizing said at least one of a plurality of arc lamps; a control unit for controlling pulse shape, amplitude, width, frequency and timing, for obtaining controllable spectral output and energy of the collimated beam through an application end of the device to a designated area of skin of the patient. The device can further comprise secondary light sources with different spectrum characteristics than the arc lamp as well as various attachments including a position feedback, material dispenser, skin cooler, and docking station for optical fiber.

12 Claims, 17 Drawing Sheets

(56) References Cited

U.S. PATENT DOCUMENTS

| | | | |
|---|---|---|---|
| 5,405,368 A * | 4/1995 | Eckhouse | 607/88 |
| 6,214,034 B1 * | 4/2001 | Azar | 607/89 |
| 6,280,438 B1 | 8/2001 | Eckhouse et al. | |
| 6,406,474 B1 * | 6/2002 | Neuberger et al. | 606/9 |
| 6,511,475 B1 * | 1/2003 | Altshuler et al. | 606/9 |
| 6,514,243 B1 | 2/2003 | Eckhouse et al. | |
| 6,824,542 B2 | 11/2004 | Jay | |
| 6,913,615 B2 * | 7/2005 | Tolkoff et al. | 607/88 |
| 2004/0133251 A1 | 7/2004 | Altshuler et al. | |
| 2004/0230258 A1 | 11/2004 | Altshuler et al. | |

OTHER PUBLICATIONS

European Patent Office, Supplementary Partial European Search Report for EP Application No. 05709147, mailed Jul. 29, 2009.

* cited by examiner

AESTHETIC TREATMENT DEVICE

CROSS-REFERENCE TO RELATED APPLICATIONS

This application is a National Phase Application of PCT International Application No. PCT/IL2005/000253, entitled "Aesthetic Treatment Device", International Filing Date Mar. 3, 2005, published on Sep. 8, 2006 as International Publication No. WO 2006/092776, which is incorporated herein by reference in its entirety.

FIELD OF THE INVENTION

The invention relates to the field of optical systems for dermatological treatment; more specifically to a method and apparatus utilizing an intense pulsed incoherent light source with integrated reflector for therapeutic and aesthetic treatment of skin disorders and hair removal.

BACKGROUND OF THE INVENTION

Electromagnetic radiation is well known in the art to be effective for skin disorders treatment and also for hair removal. Goldman in 1963 experimented with a newly invented 500 microsecond duration 694 nm wavelength ruby laser on human skin. He noted that the darker skin color absorbed more radiation and attributed the observations to selective absorption by melanin. Polla and Dover in separate studies during the 1980s demonstrated that the Q-switched ruby laser targets individual melanosomes. The damage was found to be pulse-width dependent: shorter pulses of about 100 nsec width damage melanosomes much more effectively than long pulses of about 100 microseconds. This is consistent with the theory of selective photothermolysis, which states that the pulse duration of an emitted laser wavelength must be less than the thermal relaxation time of the targeted object.

Another application of electromagnetic radiation to skin disorder treatment is removal of vascular lesions. Based upon pioneering work of Anderson and Parrish in the early 1980s, several vascular-specific laser systems were developed using principles of selective photothermolysis. Laser irradiation can selectively destroy specific chromophore targets within the skin by using a combination of appropriate wavelength and pulse duration. Pulse duration must be less than the targeted chromophore's thermal relaxation time—the time necessary for the target to cool by half of its peak temperature after laser irradiation. Since wavelengths corresponding to absorption peaks for various skin chromophores are known, absorption of laser energy can be localized without damaging neighboring structures. The targeted chromophore for vascular lesions is intravascular oxyhemoglobin, so thermal damage is largely restricted to cutaneous blood vessels. For vascular lesions treatment a variety of laser sources have been utilized, starting from a short pulse 575 nm dye laser up to 1064 nm Nd:YAG laser with tens milliseconds pulse duration. The required energy fluence for typical procedure is on the scale of 10 to 50 J/cm² with about 1 hertz repetition rate.

Laser hair removal is based on the principle of selective photothermolysis, in which energy is delivered to the treatment area in such a manner as to maximize tissue damage to the hair follicle without damaging the skin epidermis and surrounding tissue. Melanin pigment makes a logical target chromophore, because it's most abundant in the hair bulb, which is believed to be the most important target for hair removal; it's much less abundant in the epidermis, even in dark-skinned patients; and it absorbs well in the wavelength range between 600 and 1100 nm. With selective photothermolysis, both the wavelength and pulse duration should be such that laser energy will target melanin in the hair follicles without damaging the adjacent structures, including melanin in the epidermis. The optimum pulse duration should be longer than the thermal relaxation time (the time it takes for half the heat energy to be conducted away from a target tissue) of the epidermis, allowing heat energy to be conducted away, but shorter than the thermal relaxation time of the hair follicle, confining the heat to this structure. The thermal relaxation time is related to the square of the diameter of the target structure: less than 1 msec for epidermis, and 10 to 50 msec for hair follicles depending on the diameter of the hair shaft.

Cooling the skin helps to dissipate heat away from the epidermis, leaving the deeper hair follicles vulnerable. Longer pulses enhance heating and broaden the zone of thermal damage around the follicle. Typically fluences in the range of 20 to 80 J/cm² are required within a pulse or a train of few pulses with pulse width on the scale of 10 msec.

A large variety of electromagnetic radiation sources are utilized for the abovementioned procedures. Among them are diode lasers, pulsed ruby laser, Nd:YAG laser, alexandrite laser, and non-coherent flash lamp sources with appropriate spectral filters. A high energy flash lamp is disclosed in U.S. Pat. No. 6,280,438 by Eckhouse, et al, entitled "METHOD AND APPARATUS FOR ELECTROMAGNETIC TREATMENT OF THE SKIN, INCLUDING HAIR DEPILATION" (2001).

This configuration of linear flash lamp inside a reflector is commonly utilized in flash-lamp based systems for skin treatment. The flash lamp radiation is delivered to the treated area by multiple reflections from the reflector surface.

A disadvantage of this prior art system is that the reflections significantly reduce the efficiency of the light transfer from the flash lamp to the treated area.

Another disadvantage of this prior art system is that the flash lamp has to be water-cooled in order to dissipate the energy absorbed in the flash lamp tube material.

Another disadvantage of this prior art system is that the long lamp dimensions and the reflector geometry do not allow focusing of the light to smaller spot sizes with respect to the reflector output aperture.

Still another disadvantage of this prior art system is that the lamp's long arc makes it very difficult to change its output beam size by optical means.

The output spectrum of a flash lamp depends on the energy density imposed on it. The radiation of the arc lamp can be modeled by black body radiation. The radiation emitted at a given wavelength λ per unit area can be written in the following way:

$$L(\lambda) = \frac{2\pi c^2 h}{\lambda^5} \frac{1}{\exp(hc/\lambda kT) - 1},$$

where $c = 2.998 \cdot 10^8$ m s$^{-1}$ is the speed of light,
$h = 6.626 \cdot 10^{-34}$ m² kg s$^{-1}$ is Plank's constant,
$k = 1.38 \cdot 10^{-23}$ m² kg s$^{-2}$ K$^{-1}$ is Boltzmann's constant, and
T is the source temperature.

The total emitted radiation within a given spectral range is given by:

$$P = \varepsilon \int_{\lambda_1}^{\lambda_2} L(\lambda) d\lambda,$$

where ε is the source emissivity. The total emitted power is given by:

$$P_0 = \varepsilon \sigma T^4 S,$$

where $\sigma = 5.67 \cdot 10^{-8}$ J K$^{-4}$ m$^{-2}$ s$^{-1}$, and S is the source radiating area.

With reference to FIG. 1A, curves 121, 122, and 123 represent the radiation spectral distribution for various input power levels (P) for a black body source mimicking a typical flash lamp with 3 mm arc diameter and 50 mm arc length. The emissivity value of such a source is about 0.02, while the input energy to light conversion efficiency is about 90%. One can easily see that for higher input power the emission spectrum shifts towards lower wavelengths in the UV (ultra violet) region. Since only the emission within a preselected spectral band (about 550 to 1200 nm) is used for skin treatment procedures, the total system efficiency decreases the more energy is wasted in UV wavelengths.

The efficiency of a flash lamp within the 550 to 1200 nm spectral region versus the input power is shown in the FIG. 1B by curve 124. The input energy to radiation conversion efficiency in the relevant spectral region decreases for higher input power. For low input power the efficiency drop is even more dramatic. The efficiency value depends only on momentary power value and not on average power.

In order to overcome these difficulties and to improve the spectral distribution of the source, the present invention utilizes a smaller arc lamp with built-in reflector, the lamp supplied by a train of smaller pulses.

For pulsed operation of arc lamps, the pulse shape strongly deviates from a rectangular shape, due to electronic power supply design difficulties. In FIG. 2A, curve 241 shows a typical pulse shape for a prior art flash lamp operated by pulsed electronic power supply. Since the emission spectrum depends on the momentary power of the source, both the high power peak and the low power tail have very low efficiency while still consuming external energy and generating excess heat in the system. Moreover, the low power tail generates excess heat in the tissue without causing a significant effect, since its power is below the required threshold for a procedure. The high peak effect is even worse, since it can cause unwanted tissue damage while exceeding the maximum power applicable for a certain procedure.

The present invention applies a series of short pulses (plot 242 in FIG. 2A) in order to create a more temporally homogenous pulse and as a result, a more homogenous power distribution. In this way both physiological obstacles of uncontrollable power level during the pulse, as well as the system electrical and cooling efficiencies, are significantly improved.

For illustration, the efficiencies of a single pulse used in prior art (curve 241 in FIG. 2A) and the overlapping pulses train of the present invention (curve 242 in FIG. 2A) are compared. The emission intensity (using arbitrary units—AU) for both 550 to 1200 nm and 340 to 400 nm spectral windows are shown in FIG. 2B by curves 244 and 243 respectively. Due to different energy conversion efficiencies, the emission temporal profiles in both spectral ranges vary significantly.

The reason for that variance is shown in FIG. 2C by curves 246 (550 to 1200 nm) and 245 (340 to 400 nm), representing the conversion efficiencies for both ranges. While the peak power drops down after the electronic pulse maximum, the efficiency increases and this causes a long time tail in the 550 to 1200 nm range emission (curve 246). The present invention utilizes a series of short overlapping pulses similar to those in curve 242 in FIG. 2A. Due to more uniform distribution of the power, the total efficiency enhancement is in the range 20 to 50%.

Many disadvantages of prior art flash lamps, including the issues described earlier in this section, are advantageously solved in the present invention. A partial list follows:

In prior art the pulse shape and as a result the output spectrum, does not match exactly the requirements of the medical procedures and precise control of them is extremely hard to achieve because of complex electronic design. It is an object of the present invention to overcome this by applying a plurality of short pulses that enable independent control of the average power during the pulse while keeping the momentary power constant.

In prior art the life expectancy of the flash lamp was limited due to pulse shape with high peak power. It is a further object of the present invention to overcome this by employing a plurality of shorter pulses with combined power significantly lower than prior art pulses of the same energy.

In prior art the irradiated area is controlled by a mechanical shutter, causing energy losses and preventing further light concentration. It is a further object of the present invention to overcome this by providing an arc lamp with integrated reflector to produce an output light that is directional with low divergence. This design enables simple optical manipulation of light, with improved focusing, beam shaping, fiber coupling, and the like.

In prior art, the beam of light is filtered to remove undesired wavelengths. It is a further object of the present invention to provide more control of the output spectrum, thereby reducing the need to filter and improving beam efficiency.

It is yet another object of the present invention in this regard to enhance the output spectrum by providing one or more secondary light sources, thereby increasing the efficiency of the device for treatments requiring the area of the spectrum that the secondary light sources enhance.

In prior art, changing and inserting filters and fluorescence conversion elements is difficult or impossible due to the filter location in the reflector area. It is a further object of the present invention to overcome this by generating a focused, substantially collimated (parallel) beam of light that over which it is easy to attach various treatment heads comprising filters, lenses, reflectors, fiber optics, and/or various other auxiliary components.

In prior art the lamp's long arc makes it very difficult to change its output beam size by optical means. It is a further object of the present invention to overcome this by improved optical beam shape adjustment, whereby the output beam can be adjusted optically according to the needs of the treatment.

In prior art, the flash lamp utilizes water cooling for heat removal, requiring a complicated system for this purpose. It is a further object of the present invention to overcome this by employing arc lamps, thereby enabling operation at equal performance levels while using air cooling, which is much easier to provide.

In prior art, heat removal from the skin is performed by an expensive, poor-conductivity optical window, with the removal performed at the time of treatment, which can be counterproductive to the treatment. It is a further object of the present invention to overcome this by providing high-conductivity thermo-electric coolers that conduct the heat from the skin before or after the treatment.

It is yet another object of the present invention in this regard to provide one or more drum applicators in contact with the skin and containing cooling and/or therapeutic liquid or gel, thereby applying the liquid or gel as the device is moved across the skin.

In prior art, there are no effective positioning aids for accurately positioning the device as it is moved across the skin. It is a further object of the present invention to provide a position feedback device that can, when the application window is moved a predetermined amount, either notify an operator or automatically trigger the next treatment.

It is yet another object of the present invention in this regard to provide spring-mounted pins that mark points on the skin when the device is applied and which points can then orient the device window for the next application.

BRIEF DESCRIPTION OF THE INVENTION

There is thus provided in accordance with a preferred embodiment of the present invention, an aesthetic treatment device for treating the skin of a patient, the device comprising:
- at least one of a plurality of arc lamps, each arc lamp provided with a reflector for obtaining a substantially collimated beam;
- a pulse generator for generating a train of pulses of electrical energy for energizing said at least one of a plurality of arc lamps;
- a control unit for controlling pulse shape, amplitude, width, frequency and timing, for obtaining controllable spectral output and energy of the collimated beam through an application end of the device to a designated area of skin of the patient.

Furthermore, in accordance with another preferred embodiment of the present invention, the device further comprises a beam shaper attachment.

Furthermore, in accordance with another preferred embodiment of the present invention, the beam shaper attachment comprises optical mirrors.

Furthermore, in accordance with another preferred embodiment of the present invention, the device further comprises an optical filter attachment that is substantially perpendicular to the beam.

Furthermore, in accordance with another preferred embodiment of the present invention, the device is further provided with at least one of a plurality of secondary light sources, each secondary light source for generating a light beam directed at the area of the skin, with a spectral output that is different from the spectral output of said at least one of a plurality of arc lamps.

Furthermore, in accordance with another preferred embodiment of the present invention, said at least one of a plurality of secondary light sources includes at least one light source from the group of light sources comprising: laser diodes, light-emitting diodes, arc-lamps.

Furthermore, in accordance with another preferred embodiment of the present invention, the device further comprises a docking station, the docking station comprising an optical adapter for channeling the beam and at least one of a plurality of optical fibers, through which the beam is channeled and applied to the skin.

Furthermore, in accordance with another preferred embodiment of the present invention, the device further comprises a position feedback attachment attached to the application end of the device, the position feedback attachment comprising a position measurement component and a position output component, the position measurement component detecting movement of the device across the skin, the position output component determining when the detected movement reaches a predefined threshold and issuing an output signal.

Furthermore, in accordance with another preferred embodiment of the present invention, the device further comprises an indicator that is activated by the output signal and notifies a user of the device that the device has moved a predefined distance.

Furthermore, in accordance with another preferred embodiment of the present invention, the device further comprises an activation circuit activated by the output signal that activates the lamp according to predetermined parameters.

Furthermore, in accordance with another preferred embodiment of the present invention, the position measurement component is a rotary encoder.

Furthermore, in accordance with another preferred embodiment of the present invention, the position measurement component is a resolver.

Furthermore, in accordance with another preferred embodiment of the present invention, the device further comprises a material dispenser attachment attached to the application end of the device, the material dispenser attachment that is in contact with the skin when the device is in use and dispenses liquid or gel material to the skin.

Furthermore, in accordance with another preferred embodiment of the present invention, the position measurement component is integrated into the dispenser.

Furthermore, in accordance with another preferred embodiment of the present invention, the device further comprises a material dispenser attachment attached to the application end of the device, the material dispenser attachment that is in contact with the skin when the device is in use and dispenses liquid or gel material to the skin.

Furthermore, in accordance with another preferred embodiment of the present invention, the material is a cooling or therapeutic material.

Furthermore, in accordance with another preferred embodiment of the present invention, the device further comprises a skin cooling attachment attached to the application end of the device, the skin cooling attachment comprising at least one of plurality of thermo electric coolers that are in contact with the skin during treatment, thereby removing heat from the skin.

Furthermore, in accordance with another preferred embodiment of the present invention, the thermo electric cooler is located adjacent to the target area of the skin, thereby cooling an area of skin immediately before or after the beam has been applied.

Furthermore, in accordance with another preferred embodiment of the present invention, the device further comprises a beam convergence attachment attached to the application end of the device, the beam convergence attachment comprising a spacing element that controls the distance of the device from the skin as well as a lens, the beam convergence attachment producing the size of the target area on the skin as a function of the distance of the device from the skin.

There is thus also provided in accordance with a preferred embodiment of the present invention, method for an aesthetic treatment of the skin of a patient, the method comprising:
- providing an aesthetic treatment device comprising:
  - at least one of a plurality of arc lamps, each arc lamp provided with a reflector for obtaining a substantially collimated beam,
  - a pulse generator for generating a train of pulses of electrical energy for energizing said at least one of a plurality of arc lamps,
  - a control unit for controlling pulse shape, amplitude, width, frequency and timing, for obtaining controllable spectral output and energy of the collimated beam through an application end of the device to a designated area of skin of the patient;
- applying a primary light beam from the application end of the aesthetic device with a controllable light spectral output.

Furthermore, in accordance with another preferred embodiment of the present invention, the method further comprises applying at least one of a plurality of secondary light beams of different spectral output from the primary light beam.

Furthermore, in accordance with another preferred embodiment of the present invention, the method further comprises that at least one of the secondary light beams is applied before, at the same time as, or after the primary beam.

Furthermore, in accordance with another preferred embodiment of the present invention, the method further comprises:
  cooling an area of skin adjacent to the designated area of the skin before or after treatment.

Furthermore, in accordance with another preferred embodiment of the present invention, the method further comprises:
  detecting movement of the application end of the device across the skin,
  determining when the detected movement reaches a predefined threshold.

BRIEF DESCRIPTION OF THE FIGS.

The invention is described herein, by way of example only, with reference to the accompanying Figures, in which like components are designated by like reference numerals.

FIG. 1A plots radiation spectral distribution for various input power for a black body source mimicking a typical flash lamp with 3 mm arc diameter and 50 mm arc length.

FIG. 1B plots the efficiency of a flash lamp within the 550-1200 nm spectral region versus the input power FIG. 2A graphically compares the larger, more uniform, and better spectrum light pulse generated by the short train of light frequency pulses of the present invention to the typical pulse of prior art.

FIG. 2B graphically compares emission intensity for two spectral ranges.

FIG. 2C graphically compares the conversion efficiencies for the two ranges of FIG. 2B.

DETAILED DESCRIPTION OF THE INVENTION

The present invention discloses an aesthetic treatment device enabling the application of incoherent pulsed light to skin for removing hair and for treating skin diseases.

Figure 1A:
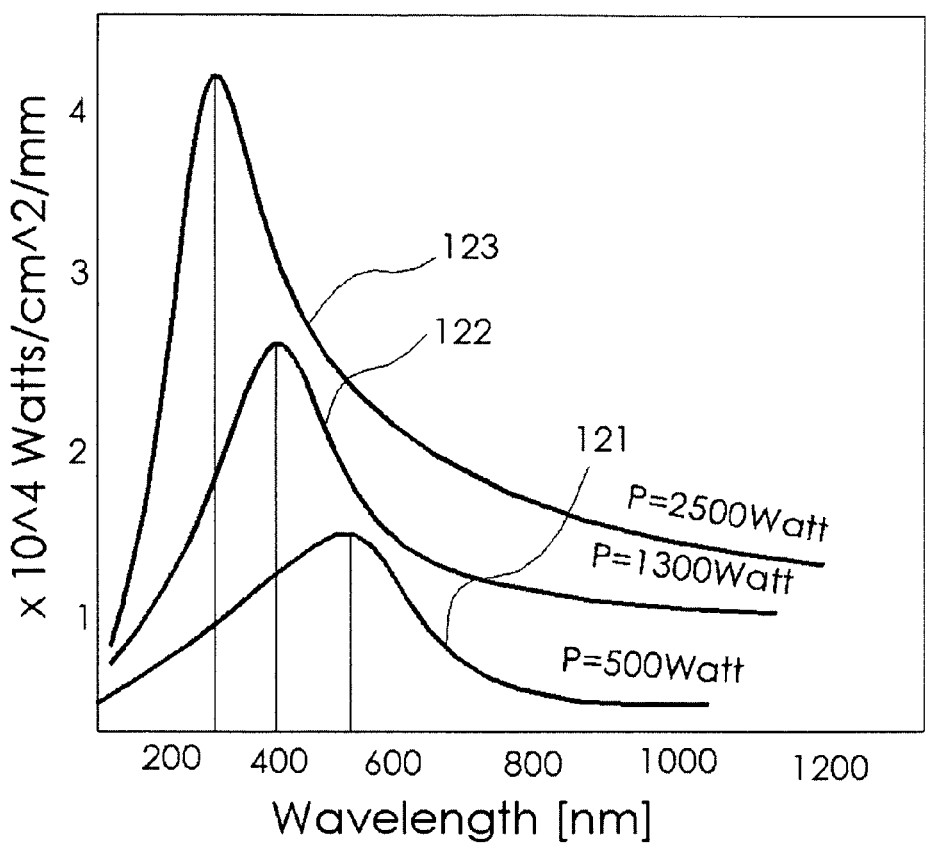
Figure 1B:
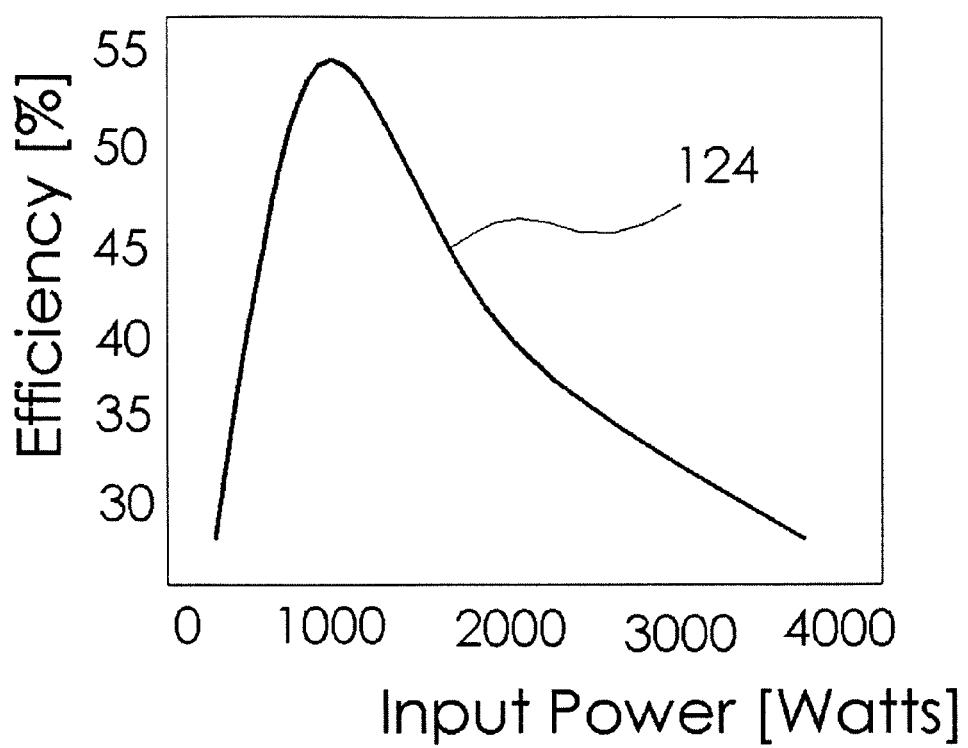
Figure 2A:
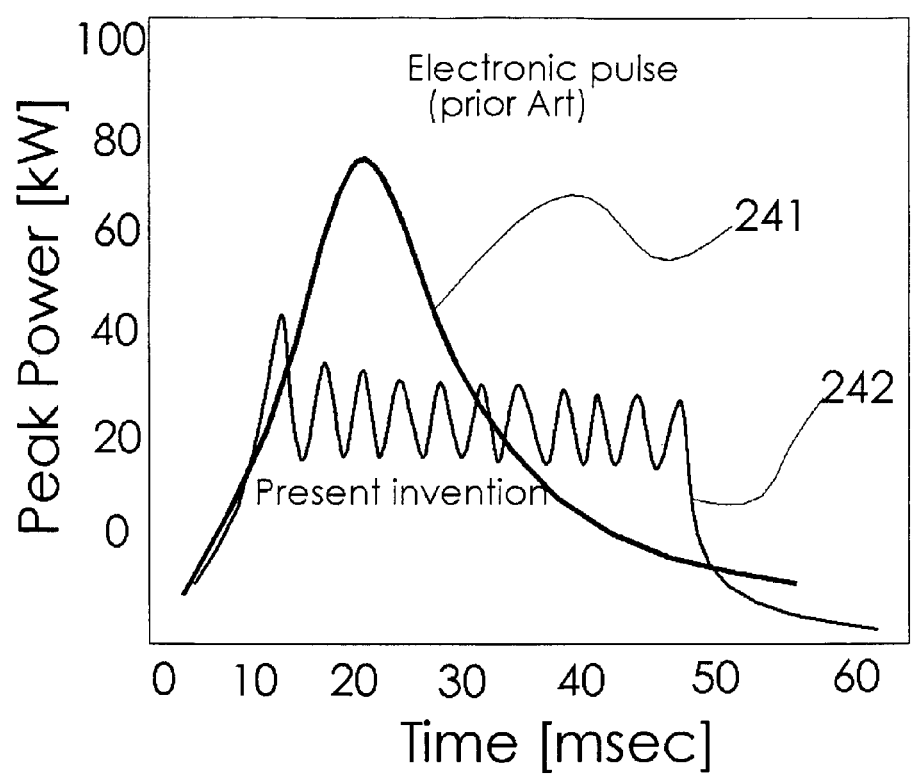
Figure 2B:
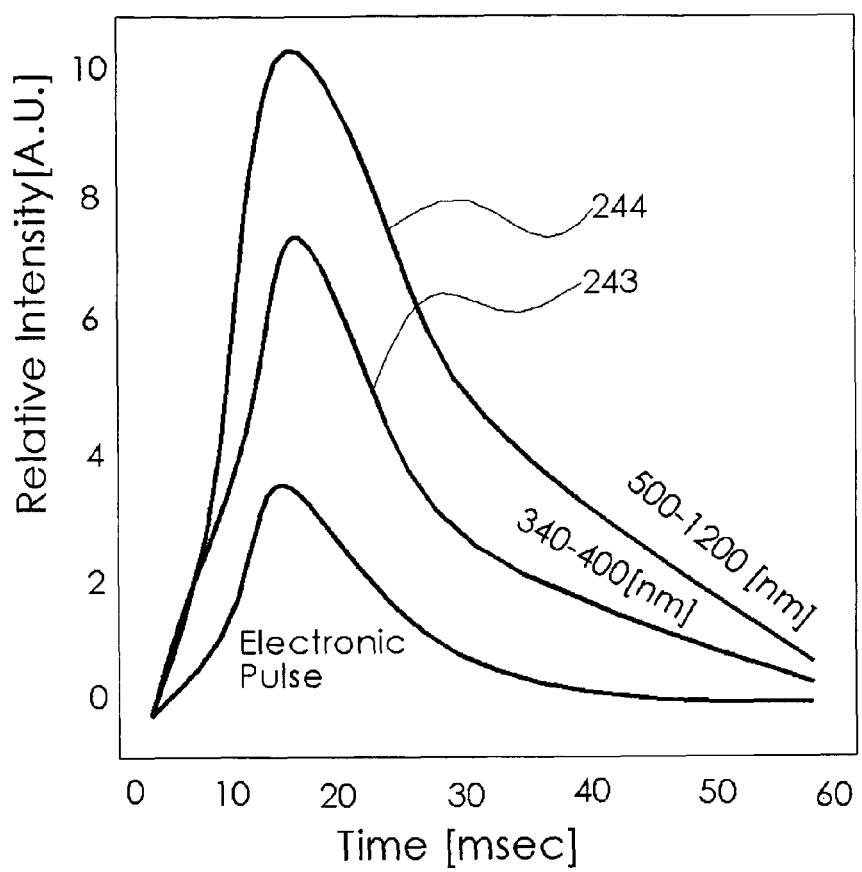
Figure 2C:
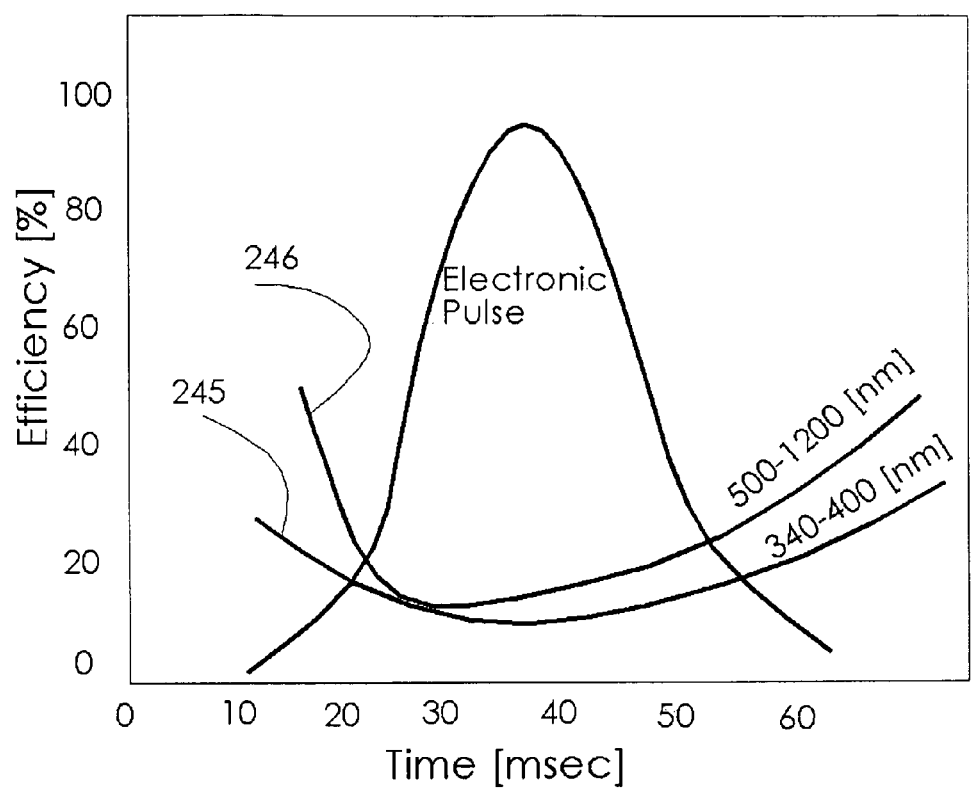
Figure 3A:
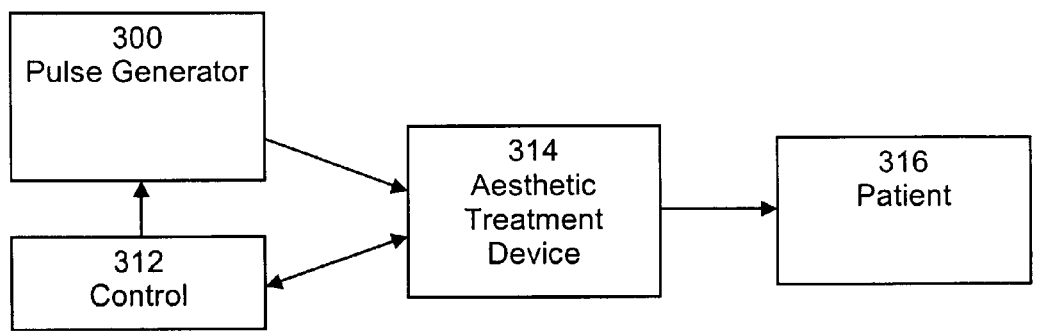
FIG. 3A is a block diagram of an aesthetic treatment system comprising an aesthetic treatment device in accordance with a preferred embodiment of the present invention.

FIG. 3A is a block diagram of an aesthetic treatment system comprising the aesthetic treatment device of the present invention. Control unit 312 controls parameters of the beam generated by aesthetic treatment device 314 and applied to the skin of patient 316. Control is effected through pulse generator 300, which supplies pulsed power to aesthetic treatment device 314. Controlled beam parameters can include intensity, duration, and other parameters known in the art. In addition, they can include parameters unique to the aesthetic treatment device 314 of the present invention, as are appropriate for device features described later in this specification. Examples of these unique parameters are lamp supply pulse train rate and intensity and position-based automated lamp triggering.

Figure 3B:
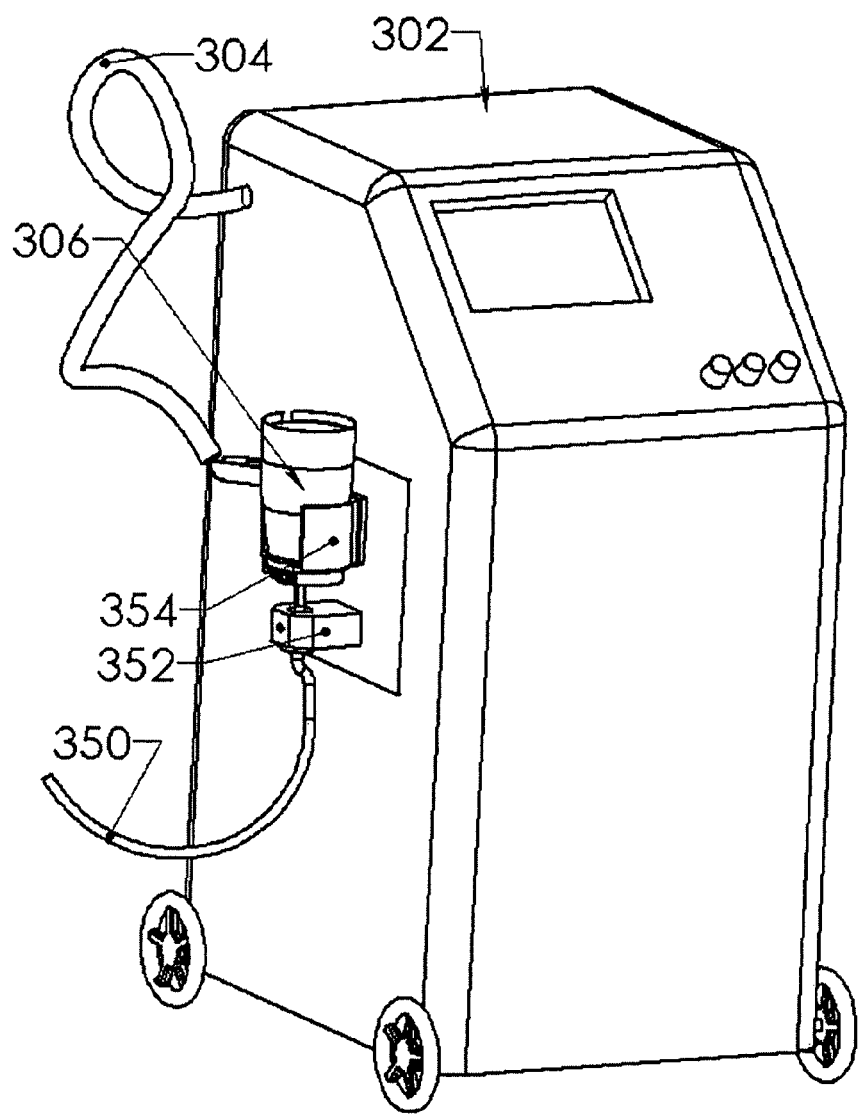
FIG. 3B is an isometric view of an aesthetic treatment system comprising an aesthetic treatment device in accordance with a preferred embodiment of the present invention.

FIG. 3B is an isometric view of an aesthetic treatment system comprising an aesthetic treatment device in accordance with a preferred embodiment of the present invention. Console 302 comprises user interface elements, such as a display and inputs, a housing for power supply and control units, and connection to power and data communication cable 304, which connects to aesthetic treatment device 306, which is stored in holder 352. Also shown is one of several treatment connectors, which can be changed according to the needs of the treatment. Shown is a docking connector 354 for connecting optical fiber light guide 350.

Figures 4A, 4B:
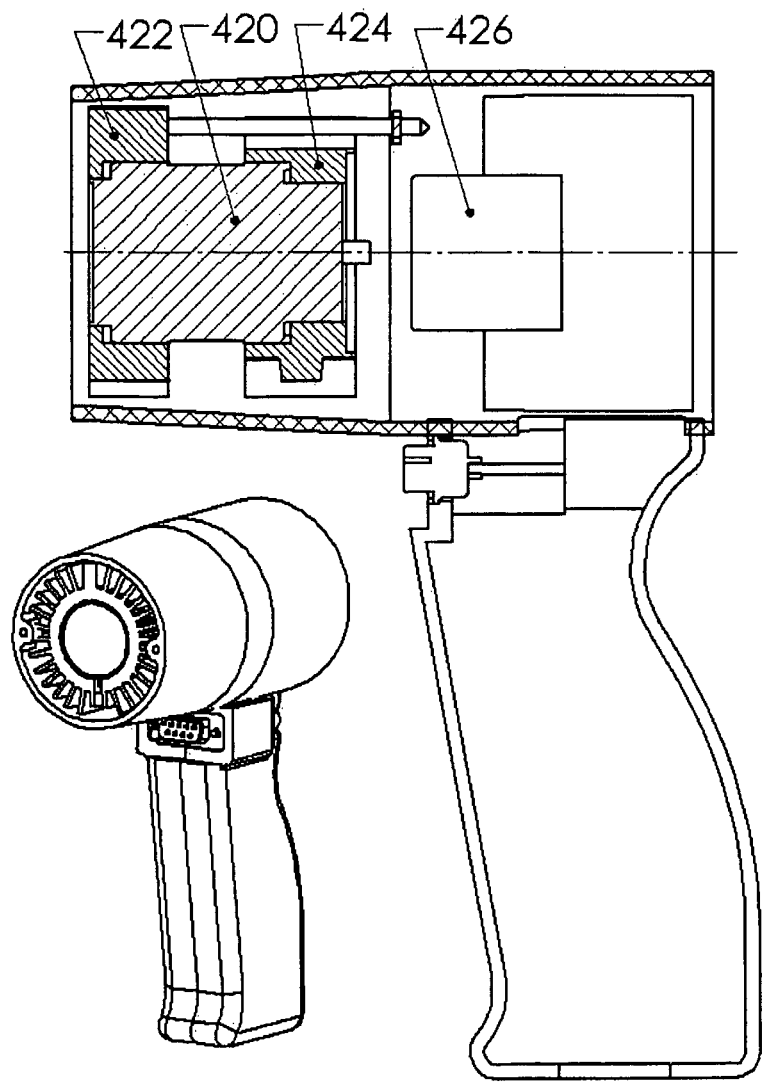
FIG. 4A is a cross-sectional side view of an aesthetic treatment device in accordance with a preferred embodiment of the present invention.
FIG. 4B is an isometric view of an aesthetic treatment device in accordance with a preferred embodiment of the present invention.

FIG. 4A and FIG. 4B illustrate the primary elements of an aesthetic treatment device 306 in accordance with a preferred embodiment of the present invention. Arc lamp 420 is cooled by lamp front heat sink 422, lamp rear heat sink 424, and fan 26.

Figure 5:
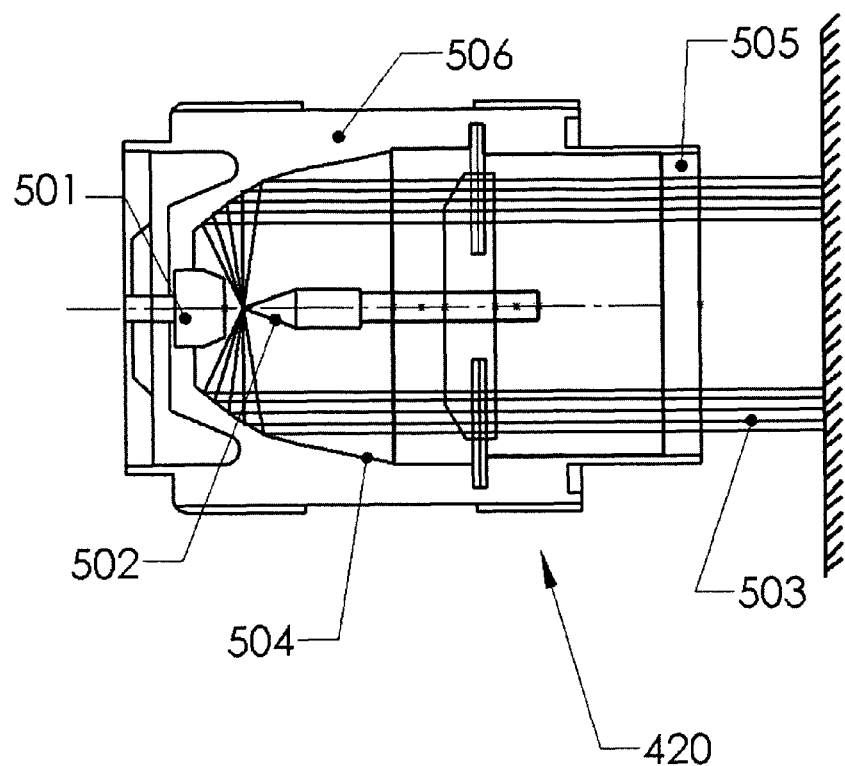
FIG. 5 is a cross-sectional side view of a representative light source with a built-in reflector for use in an aesthetic treatment device in accordance with the present invention.

An exemplary arc lamp 420 is shown in more detail in FIG. 5. The arc lamp contains one or more inert gases, such as Xenon gas. The power supply to the arc lamp is generally in the range: 100 watts-5000 watts. An arc is created between two electrodes 501 and 502 to generate an intense light pulse. The light beam represented by a bundle of rays 503 travels from the source to a built-in parabolic reflector 504 and consequently is shaped to a substantially collimated light beam to exit transparent window 505. The light beam has a basic spectrum preferably ranging from deep UV (ultra violet) around 200 nm to far IR (infra red) up to 1400 nm and the spectrum is only limited by window's 505 transparency. The denoted lamp housing 506 is built from ceramic material to increase its mechanical and thermal stability and endurance.

In a preferred embodiment of the present invention, the output spectrum of arc lamp 420 is controlled by varying the pulse shape, amplitude, width, frequency and/or timing while keeping the total energy per pulse constant. Preferably pulses have temporal widths ranging from 1 microsecond to continuous wave operation. In an alternative preferred embodiment, the arc lamp is operated by plurality of short overlapping pulses resulting in a long pulse train of 10 to 100 msec duration. In another alternative preferred embodiment, the arc lamp is operated by plurality of pulses, each having a recommended duration of 10 to 100 millisecond, energy of 5 to 100 joules, and a repetition rate on the scale of 1 Hz. In another alternative preferred embodiment, the arc lamp is operated by pulses with duration on a microsecond scale, energy on the scale of 10 joules, and a repetition rate on the scale of 1 Hz.

Figure 6:
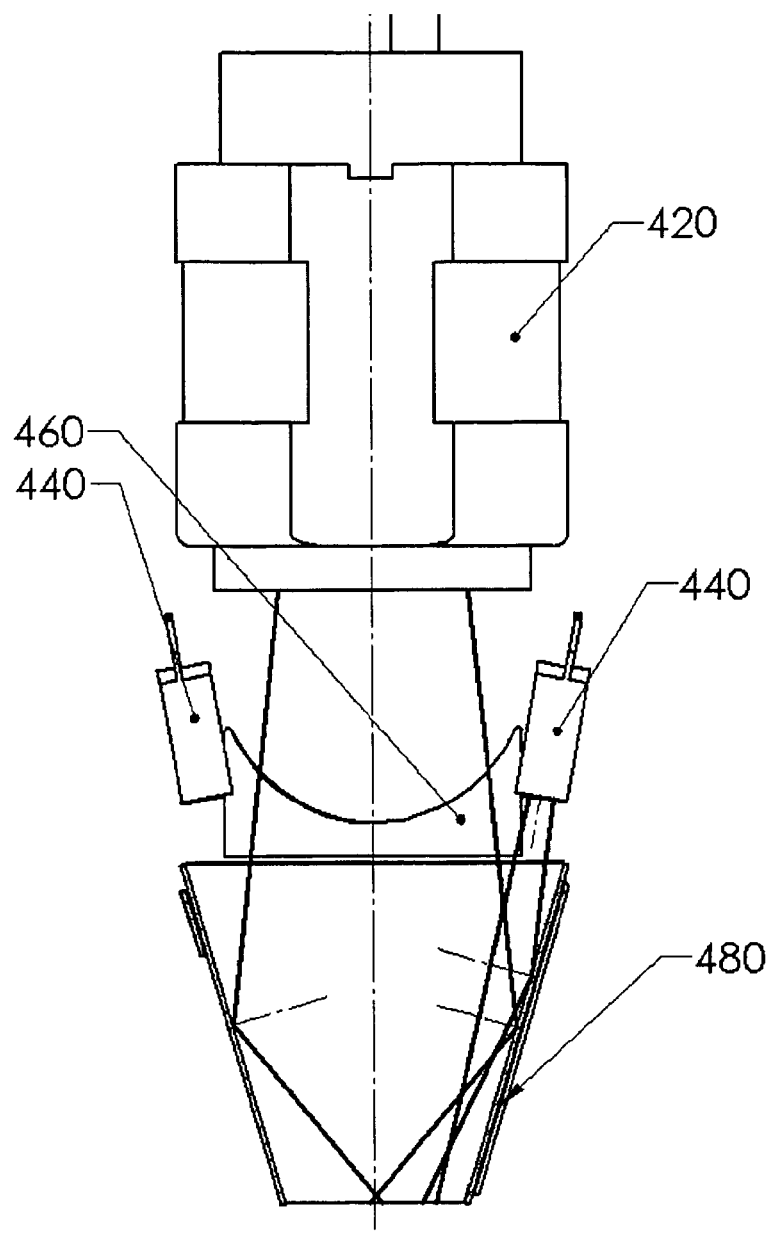
FIG. 6 is a cross-sectional top view of an aesthetic treatment device augmented by secondary light sources in accordance with an alternative preferred embodiment of the present invention.

An alternative preferred embodiment of aesthetic treatment device 306 comprises at least one of a plurality of secondary light sources with a spectral output that is different from the spectral output of arc lamp 420 and which can be applied before, at the same time as, or after applying arc lamp 420. FIG. 6 is a top view of an aesthetic treatment device 306 comprising arc lamp 420 further augmented by secondary light sources 440. The beam from lamp 420 passes through cylindrical lens 460 and is combined with the beam from secondary light sources 440 by beam-combining mirrors 480.

Examples of secondary light sources 440 are laser diodes (shown in FIG. 6), light emitting diodes (LEDs), or other arc lamps with different beam spectrums.

Figure 7:
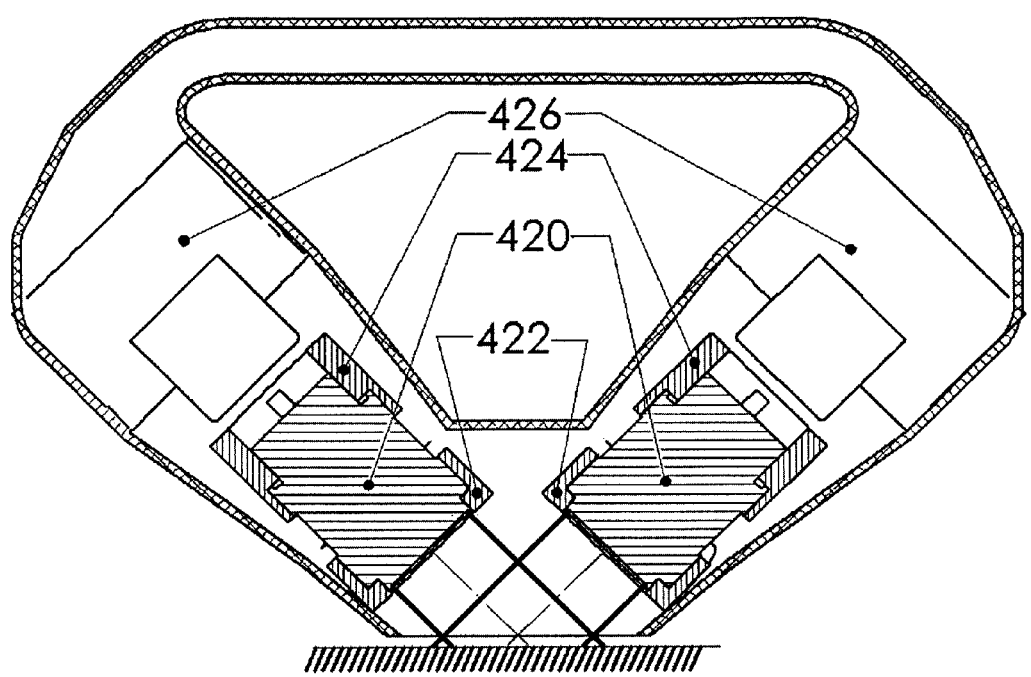
FIG. 7 is a cross-sectional side view of an alternative embodiment of an aesthetic treatment device comprising two arc lamps with different beam spectrums.

An alternative preferred embodiment of aesthetic treatment device 306 comprises is shown in FIG. 7, comprising two arc lamps with different beam spectrums. Arc lamps 420 are cooled by front heat sinks 422, rear heat sinks 424, and cooling fans 426. The arc lamps can have the same or different spectral outputs and can be applied at the same time, in overlapping time, or in succession.

The secondary light sources enhance the output beam spectrum by changing the amount of light in a given region of the spectrum. The operation of the light sources can be independent on the time scale.

Various attachments can be attached at the application end (where the beam exits the device) of aesthetic treatment device 314 using a quick release mechanism, such as a bayonet or twist-lock connection.

Some attachments shape the substantially collimated beam generated by arc lamp 420 and built-in parabolic reflector 504. Others provide improvements to device operation.

Figure 8:
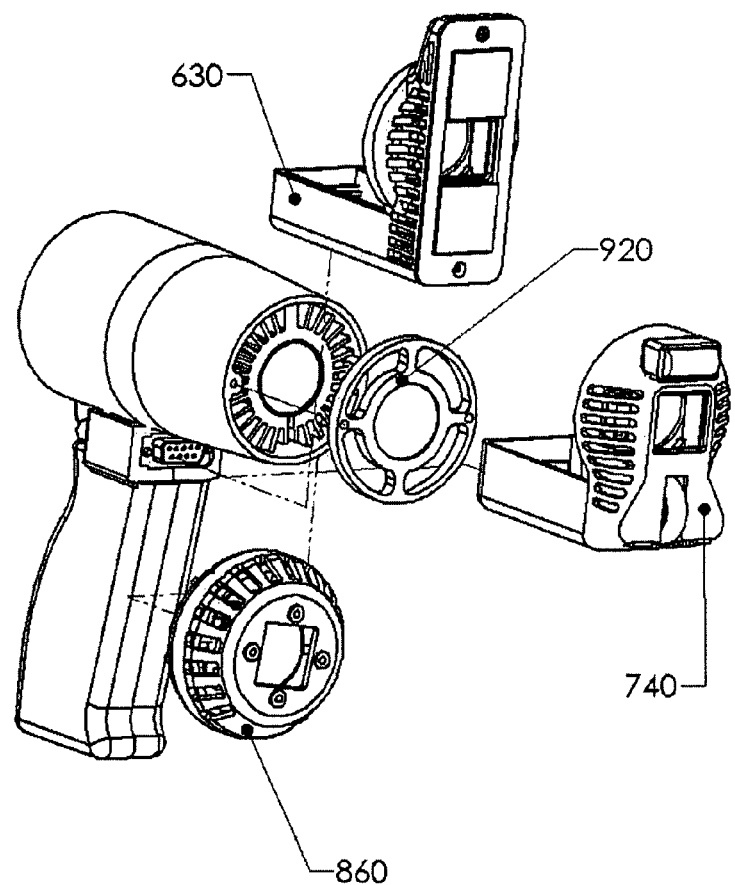
FIG. 8 is an isometric view of various attachments that can be attached at the application end of aesthetic treatment device.

Several attachments are shown in FIG. 8, including an attachment 630 for cooling the skin immediately before and after treatment (described in greater detail later in this specification), an attachment 740 for position feedback and/or for dispensing materials on the skin (also described in greater detail later in this specification), an attachment 920 for filtering the beam, and an attachment 860 comprising mirrors for shaping the beam into a square of rectangular footprint.

Filtering attachment 920 comprises at least one of a plurality of filters oriented substantially perpendicular to the beam.

Beam shaping attachment 860 can comprise a set of mirrors for shaping the beam into a square footprint or it can combine a cylindrical lens in combination with a set of mirrors to shape the beam into a rectangular footprint.

Filtering attachment 920 and/or beam shaping attachment 860 can be used by themselves or in combination with other attachments.

Figures 9A, 9B:
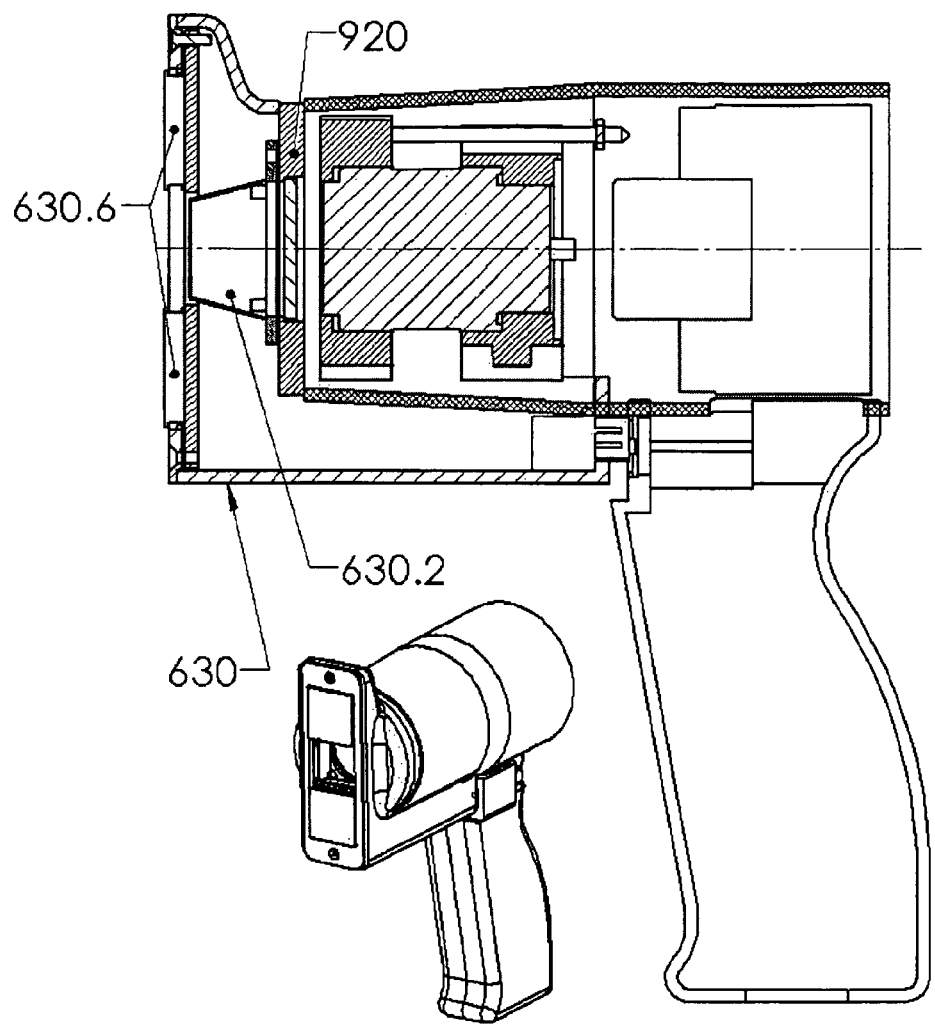
FIG. 9A is a cross-sectional side view of an aesthetic treatment device fitted with a skin cooling attachment in accordance with a preferred embodiment of the present invention.
FIG. 9B is an isometric view of an aesthetic treatment device fitted with a skin cooling attachment in accordance with a preferred embodiment of the present invention.

FIG. 9A and FIG. 9B illustrate an aesthetic treatment device fitted with a filter attachment 920 and a skin cooling attachment 630 in accordance with a preferred embodiment of the present invention. Skin cooling attachment 630 includes at least one of plurality of thermo electric coolers (TECs) 630.6, which are solid state cooling devices that create, via thermoelectric effect, heat flux between the junction of two different types of materials, thereby cooling the skin that is in contact with the cooling side of the TECs. Prior art could not use these TECs since prior art requires that the treatment device be as close as possible to the skin. Skin cooling attachment 630 fits over filter 920, which filters the light beam, followed by mirrors 630.2 which shape the beam, and TECs 630.6, which cool the skin before and after application of the beam.

Figures 10A, 10B:
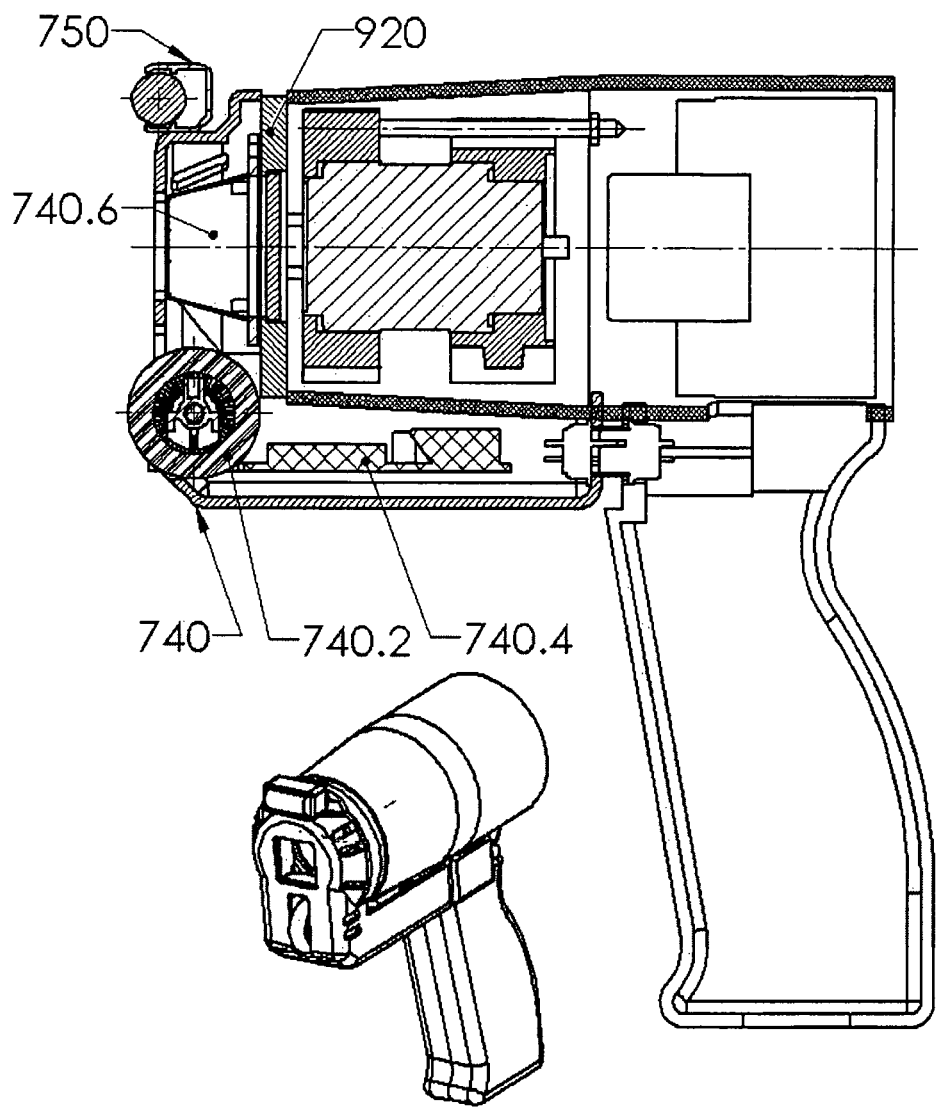
FIG. 10A is a cross-sectional side view of an aesthetic treatment device fitted with a position feedback component and a material dispenser in accordance with a preferred embodiment of the present invention.
FIG. 10B is an isometric view of an aesthetic treatment device fitted with a position feedback component and a material dispenser in accordance with a preferred embodiment of the present invention.

FIG. 10A and FIG. 10B illustrate an aesthetic treatment device fitted with attachment 740 for position feedback and/or for dispensing materials on the skin. (Alternatively, either of these components could be mounted alone on the attachment.) Mirrors 740.6 concentrate the beam. Position measuring device 740.2 with associated control circuitry 740.4 is preferably a rotary optical encoder, although it could be a resolver or other position measurement device. Position measuring device 740.2 is integrated with a component that detects movement of aesthetic treatment device 314. Preferably this component is a wheel in contact that is rotated by contact with the skin when aesthetic treatment device 314 is moved. Preferably the feedback can be configured to signal when the aperture of the aesthetic treatment device 314 has moved a distance equal to its own size. In other words, if the aperture is 2 cm wide, the signal will be generated when position feedback component 740 has turned 2 cm, indicating that the aesthetic treatment device has moved just enough that it now covers the next area to be treated (the area immediately adjacent to the area that has just been treated). If the treatment is being controlled manually, the signal can be an audible signal for the operator. If the treatment is being controlled automatically, the signal can trigger the beam.

A material dispenser 750 can be implemented in various ways as will be familiar to one skilled in the art. In the exemplary implementation of FIG. 10 it comprises a drum that is rotated by the skin when aesthetic treatment device 314 is moved. Material dispenser 750 holds a gel or liquid and can dispense its contents as it rotates or as triggered by position measuring device 740.2. Material dispenser 750 can be used to dispense therapeutic material or cooling material, for example cold water. Depending on the requirements for the application, material dispenser 750 could be made from reusable or disposable materials.

Figure 11A:
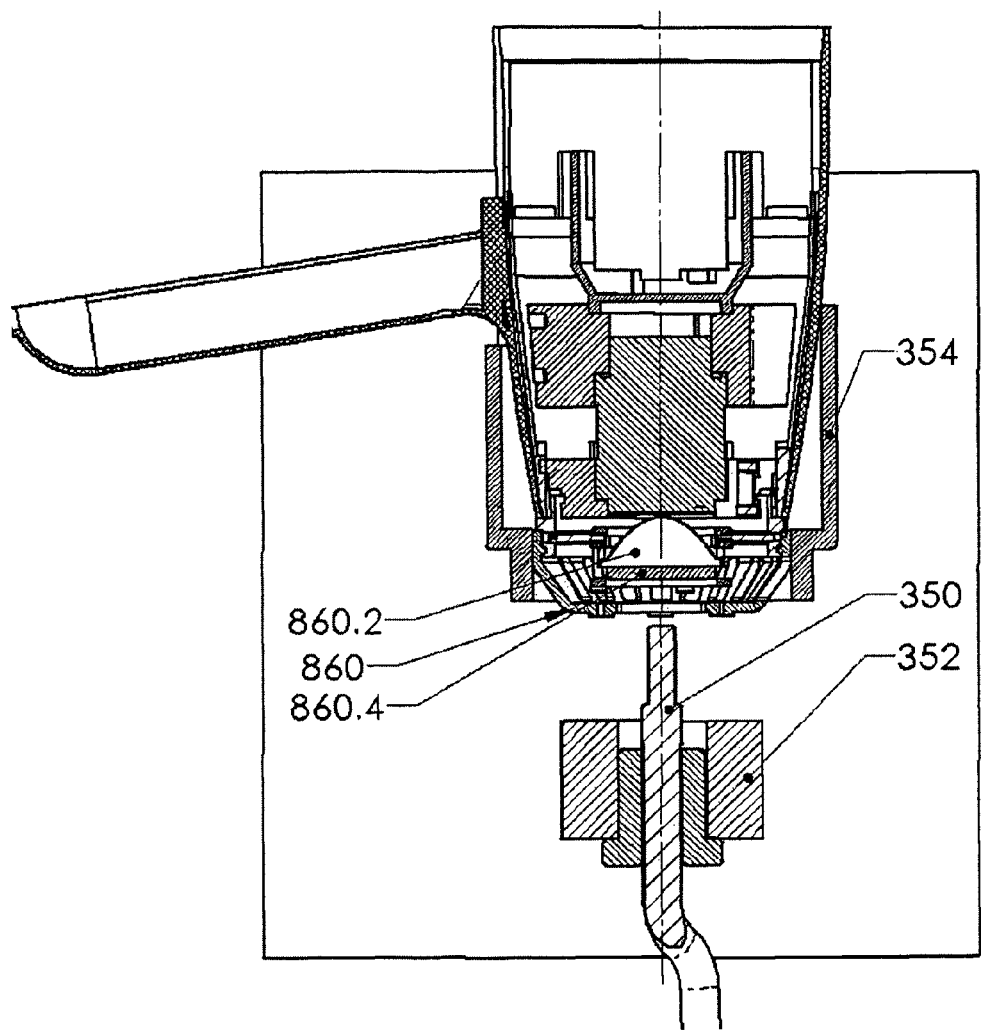
FIG. 11A is a cross-sectional side view of an aesthetic treatment device fitted with an optical fiber interface in accordance with a preferred embodiment of the present invention.
Figure 11B:
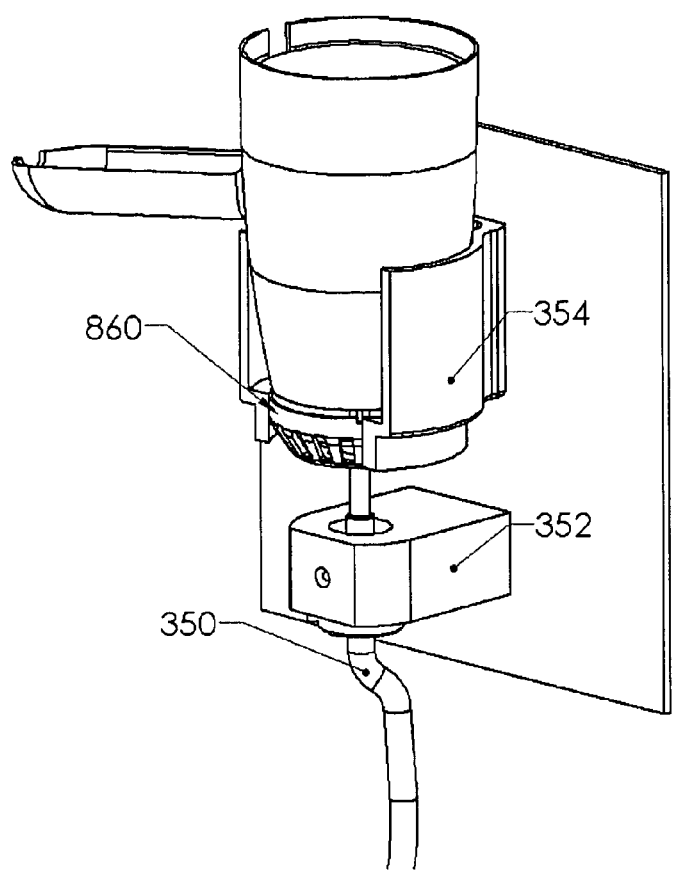
FIG. 11B is an isometric view of an aesthetic treatment device fitted with an optical fiber interface in accordance with a preferred embodiment of the present invention.

FIG. 11A and FIG. 11B illustrate an aesthetic treatment device 314 fitted with an optical fiber interface in accordance with a preferred embodiment of the present invention. The interface serves to channel the output beam into the proximal end of an optical fiber or a cable comprised of optical fibers. In a preferred embodiment, aesthetic treatment device 314 is fitted with focusing attachment 860 and held in docking station 354. Focusing attachment 860 comprising lens 860.2 and filter 860.4 focuses the light beam into light guide 350, which comprises one or more optical fibers and which is held in light guide holder 352. The beam is then available at the distal end of light guide 350, which is particularly useful for difficult to access locations, such as the ear holes, the nostrils, and fine defects in the skin.

Figure 12:
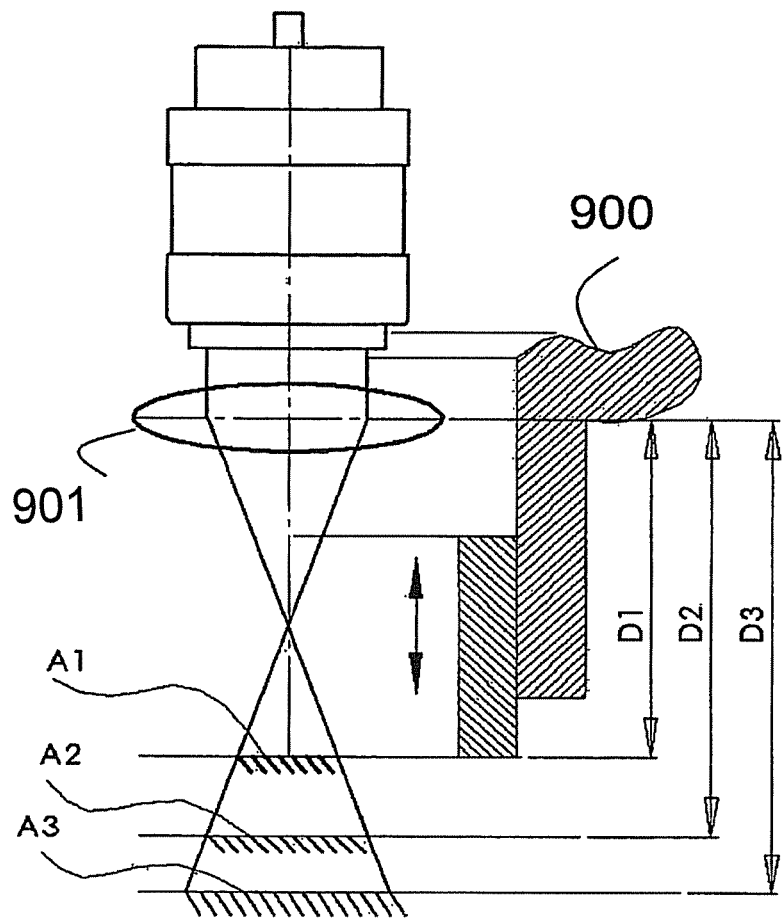
FIG. 12 is a cross-sectional side view of a beam convergence attachment for an aesthetic treatment device in accordance with a preferred embodiment of the present invention.

FIG. 12 illustrates a beam convergence attachment, which attaches to the application end of the device and controls beam convergence. Spacing element 900 controls the distance of the device from the skin and converging lens 901 converges the beam on the target area. The larger the distance set by spacing element 900 (for example, D1, D2, or D3.) the larger the target area (for example, A1, A2, or A3, respectively).

It should be clear that the description of the embodiments and attached Figures set forth in this specification serves only for a better understanding of the invention, without limiting its scope as covered by the following Claims.

It should also be clear that a person skilled in the art, after reading the present specification could make adjustments or amendments to the attached Figures and above described embodiments that would still be covered by the following Claims.

The invention claimed is:

1. An aesthetic treatment device for treating the skin of a patient, the device comprising:
    at least one of a plurality of arc lamps, each arc lamp provided with a reflector for obtaining a substantially collimated beam;
    a pulse generator for generating a train of pulses of electrical energy for energizing the at least one of a plurality of arc lamps;
    a control unit for controlling pulse shape, amplitude, width, frequency and timing, for obtaining controllable spectral output and energy of the collimated beam through an application end of the device to a designated area of the skin of the patient;
    at least one of a plurality of secondary light sources, each secondary light source for generating a light beam directed at the area of the skin, with spectral output that is different from spectral output of the at least one of a plurality of arc lamps, wherein the at least one of a plurality of secondary light source includes at least one laser diode; and
    a position feedback attachment attached to the application end of the device, the position feedback attachment comprising a position measurement component and a position output component, the position measurement component detecting movement of the device across the skin, the position output component determining when the detected movement reaches a predefined threshold and issuing an output signal.

2. The device of claim 1, further comprising an indicator that is activated by the output signal and notifies a user of the device that the device has moved a predefined distance.

3. The device of claim 1, further comprising an activation circuit activated by the output signal that activates the at least one of a plurality arc lamps according to predetermined parameters.

4. The device of claim 1, wherein the position measurement component is a rotary encoder.

5. The device of claim 1, wherein the position measurement component is a resolver.

6. The device of claim 1, further comprising a material dispenser attachment attached to the application end of the device, the material dispenser attachment configured to be in contact with the skin when the device is in use and dispenses liquid or gel material to the skin.

7. The device of claim 6, wherein the position measurement component is integrated into the material dispenser attachment.

8. The device of claim 6, wherein the liquid or gel material is a cooling or therapeutic material.

9. An aesthetic treatment device for treating the skin of a patient, the device comprising:
    at least one of a plurality of arc lamps, each arc lamp provided with a reflector for obtaining a substantially collimated beam;
    a pulse generator for generating a train of pulses of electrical energy for energizing the at least one of a plurality of arc lamps;
    a control unit for controlling pulse shape, amplitude, width, frequency and timing, for obtaining controllable spectral output and energy of the collimated beam through an application end of the device to a designated area of the skin of the patient;
    at least one of a plurality of secondary light sources, each secondary light source for generating a light beam directed at the area of the skin, with spectral output that is different from spectral output of the at least one of a plurality of arc lamps, wherein the at least one of a plurality of secondary light source includes at least one laser diode; and
    a docking station, the docking station comprising an optical adapter for channeling the beams and at least one of a plurality of optical fibers, through which the beams is are channeled and applied to the skin.

10. An aesthetic treatment device for treating the skin of a patient, the device comprising:
    at least one of a plurality of arc lamps, each arc lamp provided with a reflector for obtaining a substantially collimated beam;
    a pulse generator for generating a train of pulses of electrical energy for energizing the at least one of a plurality of arc lamps;
    a control unit for controlling pulse shape, amplitude, width, frequency and timing, for obtaining controllable spectral output and energy of the collimated beam through an application end of the device to a designated area of the skin of the patient;
    at least one of a plurality of secondary light sources, each secondary light source for generating a light beam directed at the area of the skin, with spectral output that is different from spectral output of the at least one of a plurality of arc lamps, wherein the at least one of a plurality of secondary light source includes at least one laser diode; and
    a material dispenser attachment attached to the application end of the device, the material dispenser attachment configured to be in contact with the skin when the device is in use and dispenses liquid or gel material to the skin.

11. An aesthetic treatment device for treating the skin of a patient, the device comprising:
    at least one of a plurality of arc lamps, each arc lamp provided with a reflector for obtaining a substantially collimated beam;
    a pulse generator for generating a train of pulses of electrical energy for energizing the at least one of a plurality of arc lamps;
    a control unit for controlling pulse shape, amplitude, width, frequency and timing, for obtaining controllable spectral output and energy of the collimated beam through an application end of the device to a designated area of the skin of the patient;
    at least one of a plurality of secondary light sources, each secondary light source for generating a light beam directed at the area of the skin, with spectral output that is different from spectral output of the at least one of a plurality of arc lamps, wherein the at least one of a plurality of secondary light source includes at least one laser diode; and
    a beam convergence attachment attached to the application end of the device, the beam convergence attachment comprising a spacing element that controls the distance of the device from the skin as well as a lens, the beam convergence attachment producing the size of the target area on the skin as a function of the distance of the device from the skin.

12. A method for an aesthetic treatment of the skin of a patient, the method comprising:
   providing an aesthetic treatment device comprising:
   at least one of a plurality of arc lamps, each arc lamp provided with a reflector for obtaining a substantially collimated beam,
   a pulse generator for generating a train of pulses of electrical energy for energizing said at least one of a plurality of arc lamps,
   a control unit for controlling pulse shape, amplitude, width, frequency and timing, for obtaining controllable spectral output and energy of the collimated beam through an application end of the device to a designated area of skin of the patient;
   at least one of a plurality of secondary light sources, each secondary light source for generating a light beam directed at the area of the skin, with spectral output that is different from spectral output of the at least one of a plurality of arc lamps, wherein the at least one of a plurality of secondary light source includes at least one laser diode;
   applying at least one primary light beam from the at least one of a plurality of arc lamps and at least one secondary light beam from the at least one of a plurality of secondary light sources from the application end of the aesthetic device with a controllable light spectral output to a designated area of the skin; and
   detecting movement of the application end of the device across the skin, determining when the detected movement reaches a predefined threshold.

* * * * *